US007960106B2

(12) United States Patent
Nikkari et al.

(10) Patent No.: US 7,960,106 B2

(45) Date of Patent: Jun. 14, 2011

(54) DIAGNOSTIC METHOD AND PRODUCTS USEFUL THEREIN

(75) Inventors: Simo Nikkari, Turku (FI); Tuukka Skottman, Helsinki (FI); Mikael Skurnik, Masala (FI)

(73) Assignee: The Finnish Defence Forces, Helsinki (FI)

( * ) Notice: Subject to any disclaimer, the term of this patent is extended or adjusted under 35 U.S.C. 154(b) by 892 days.

(21) Appl. No.: 11/634,154

(22) Filed: Dec. 6, 2006

(65) Prior Publication Data

US 2011/0117543 A1 May 19, 2011

(30) Foreign Application Priority Data

Dec. 8, 2005 (FI) ..................................... 20055654

(51) Int. Cl.
*C12Q 1/68* (2006.01)

(52) U.S. Cl. .......................................................... 435/6

(58) Field of Classification Search ........................ None
See application file for complete search history.

(56) References Cited

U.S. PATENT DOCUMENTS

| | | | | |
|---|---|---|---|---|
| 6,329,156 | B1 * | 12/2001 | Cirino et al. | 435/7.21 |
| 7,695,941 | B2 * | 4/2010 | Lin et al. | 435/91.2 |
| 2003/0082563 | A1 * | 5/2003 | Bell et al. | 435/6 |
| 2004/0185438 | A1 | 9/2004 | Ecker | |
| 2004/0259226 | A1 | 12/2004 | Robey et al. | |

FOREIGN PATENT DOCUMENTS

| | | | |
|---|---|---|---|
| WO | WO 03/075837 | A2 | 9/2003 |
| WO | WO 2004/070001 | A2 | 8/2004 |
| WO | WO 2005/030991 | A1 | 4/2005 |

OTHER PUBLICATIONS

Buck et al ("Design Strategies and Performance of Custom DNA Sequencing Primers" Biotechniques. 1999. 27(3): pp. 528-536.*

Lowe et al. (Nucleic Acids Research, vol. 18, No. 7, p. 1757-1761, 1990).*

Wilson et al. ("A multiplexed PCR-coupled liquid bead array for the simultaneous detection of four biothreat agents" Molecular and Cellular Probes, Academic Press, London, GB, vol. 19, No. 2, Apd12005 (Apr. 2005), pp. 137-144).*

Loiez et al. ("Detection of Yersinia pestis in Sputum by Real-Time PCR" Journal of Clinical Microbiology, vol. 41, No. 10, Oct. 2003, pp. 4873-4875).*

Versage et al. ("Development of multitarget Real-Time TaqMan PCR assay for enhanced detection of *Francisella tularensis* in complex specimens" Journal Ofclinical Microbiology, vol. 41, No. 12, Dec. 2003, pp. 5492-5499).*

GENBANK Accession Nos. M27820 (Apr. 26, 1993).*

GENBANK Accession Nos. Y08861 (Feb. 16, 1997).*

Charrel, R.N. et al., "Multi-Pathogens Sequence Containing Plasmids as Positive Controls for Universal Detection of Potential Agents of Bioterrorism," BMC Micorbiology, vol. 4, pp. 1-11, 2004.

Loiez e, C. et al., "Detection of Yersinia Pestis in Sputum by Real-Time PCR," Journal of Clinical Microbiology, vol. 41, No. 10, pp. 4873-4875 Oct. 2003.

Versage, J.L. et al., "Development of a Multitarget Real-Time TaqMan PCR Assay for Enhanced Detection of *Francisella tularensis* in Complex Specimens," Journal of Clinical Microbiology, vol. 41, No. 12, pp. 5492-5499, Dec. 2003.

Ellerbrok, Heinz et al. "Rapid and sensitive identification of pathogenic and apathogenic *Baccilus anthracis* by real-time PCR", *FEMS*, Letters, vol. 214, pp. 51-59, 2002.

Hanna, P. "Anthrax Pathogenesis and Host Response", *Curr. Top. Microbiol. Immunol.*, vol. 225, pp. 13-35, 1988.

Bastien, M. et al. "A Specific, Sensitive and Rapid (<1hr) Assay for the Detection of the Biothreat Agent *Francisella tularcusis*", Abstracts, ASM Biodefense Research Meeting, 2005.

Reif, Timothy C. et al. "Identification of Capsule-Forming *Baccillus anthracis* Spores with the PCR and a Novel Dual-Probe Hybridization Format", *Applied and Environmental Microbiology*, vol. 60, No. 5, pp. 1622-1625, May 1994.

Dokusova, Lucia et al. "Confirmation of anthrax occurrence using real-time PCR", *Biologia, bratislava*, vol. 59, No. 6, pp. 803-807, Nov. 2004.

Wilson, Wendy et al. "A multiplexed PCR-coupled liquid bead array for the simultaneous detection of four biothreat agents", *Molecular and Cellular Probes*, vol. 19, No. 2, pp. 137-144, Apr. 2005.

Chase, C.J. et al. "Real-Time PCR Assays Targeting a Unique Chromosomal Sequence for *Yersinia pestis*", *Clin. Chem.*, Aug. 11, 2005.

Bell, Constance A. et al. "Detection of *Bacillus anthracis* DNA by LightCycler PCR", *Journal of Clinical Microbiology*, vol. 40, No. 8, pp. 2897-2902, Aug. 2002.

Emanuel, P. A. et al. "Detection of *Francisella tularenis* within infected mouse tissues by using a hand-held PCR thermocycler", *J. Clin. Microbiol.*, vol. 41, No. 2, pp. 689-693, Feb. 2003.

Mandira, Varma-Basil. "Molecular Beacons fo rMultiplex Detection of Four Bacterial Bioterrorism Agents", *Clinical Chemistry*, vol. 50, No. 6, pp. 1060-1063, 2004.

Hurtle et al., "Detection of the *Bacillus anthracis gyrA* Gene by Using a Minor Groove Binder Probe", Journal of Clinical Microbiology, vol. 42, No. 1, pp. 179-185, 2004.

Jun. 11, 2010 European Office Action issued in European Patent Application No. 06 125 578.2.

* cited by examiner

*Primary Examiner* — Christopher M. Babic

(74) *Attorney, Agent, or Firm* — Oliff & Berridge, PLC

(57) ABSTRACT

A method for simultaneous detection and identification of *Bacillus anthracis, Yersinia pestis* and *Francisella tularensis*, in a single real time PCR assay using species-specific primers and Taqman MGB probes. Also, a kit for the diagnosis of bacterial bioterrorism agents. In addition, an infection-free control plasmid to verify the result of the real time PCR analysis method.

9 Claims, 3 Drawing Sheets

FIGURE 1

| Species | No. | Strain |
| --- | --- | --- |
| *Y.pestis* | | EV76-c (-"-) * |
| *Y.pestis* | | KIM M YP D1* |
| *E.coli (Y.p pla)* | | C600/pYET6* |
| *F.tularensis* | | LVS (ATCC 29684) |
| *B.anthracis* | | ATCC 4229 |
| *B.anthracis* | | Sterne 7702 |
| *Y.pseudotuberculosis* | y1 | 104§ |
| *Y.pseudotuberculosis* | y2 | 260§ |
| *Y.pseudotuberculosis* | y3 | Y.PT/8§ |
| *Y.pseudotuberculosis* | y4 | H305-36/89§ |
| *Y.pseudotuberculosis* | y5 | H1743§ |
| *Y.pseudotuberculosis* | y6 | 2947§ |
| *Y.pseudotuberculosis* | y7 | 2884§ |
| *Y.pseudotuberculosis* | y8 | Tniguchi-water§ |
| *Y.pseudotuberculosis* | y9 | No.5§ |
| *Y.pseudotuberculosis* | y10 | No.90§ |
| *Y.pseudotuberculosis* | y11 | 93221§ |
| *Y.pseudotuberculosis* | y12 | 379§ |
| *Y.pseudotuberculosis* | y13 | C119§ |
| *Y.pseudotuberculosis* | y14 | KP1244-2B§ |
| *Y.pseudotuberculosis* | y15 | 446§ |
| *Y.pseudotuberculosis* | y16 | Vlassel§ |
| *Y.pseudotuberculosis* | y17 | 579§ |
| *Y.pseudotuberculosis* | y18 | MW1003-1§ |
| *Y.pseudotuberculosis* | y19 | 323 tarm§ |
| *Y.pseudotuberculosis* | y20 | OK6011§ |
| *Y.pseudotuberculosis* | y21 | 1194§ |
| *Y.pseudotuberculosis* | y22 | WP-931110§ |
| *Y.pseudotuberculosis* | y23 | AZ960106-1§ |
| *Y.pseudotuberculosis* | y24 | 52§ |
| *Y.pseudotuberculosis* | y25 | 22917/2L§ |
| *Y.pseudotuberculosis* | y26 | Toyama 60§ |
| *Y.pseudotuberculosis* | y27 | OK6609§ |
| *Y.pseudotuberculosis* | y28 | MW151-1§ |
| *Y.pseudotuberculosis* | y29 | R103-2§ |
| *Y.pseudotuberculosis* | y30 | RD22§ |
| *Y.pseudotuberculosis* | y31 | TE-93081§ |
| *Y.pseudotuberculosis* | y32 | TU-19951a§ |
| *Y.pseudotuberculosis* | y33 | 257* |
| *Y.pseudotuberculosis* | y34 | Wla872* |
| *Y.pseudotuberculosis* | y35 | No.141* |
| *Y.pseudotuberculosis* | y36 | R2096-1§ |
| *Y.pseudotuberculosis* | y37 | R708* |
| *Y.pseudotuberculosis* | y38 | MW332-1§ |
| *Y.pseudotuberculosis* | y39 | Y25§ |
| *Y.pseudotuberculosis* | y40 | 6088§ |
| *Y.pseudotuberculosis* | y41 | R2031§ |
| *Y.pseudotuberculosis* | y42 | MW109-2§ |
| *Y.pseudotuberculosis* | y43 | WP-930601§ |
| *Y.pseudotuberculosis* | y44 | J92§ |
| *Y.pseudotuberculosis* | y45 | N916* |
| *Y.pseudotuberculosis* | y46 | 12-219N1§ |
| *Y.pseudotuberculosis* | y47 | SP-930602§ |
| *Y.pseudotuberculosis* | y48 | WP-931201§ |

| Species | No. | Strain |
| --- | --- | --- |
| *Y. bercovieri* | 1 | 3016/84* |
| *Y. bercovieri* | 2 | 127/84* |
| *Yersinia ruckeri* | 3 | RS41* |
| *Y. mollareti* | 4 | 92/84* |
| *Y. mollareti* | 5 | IP 22404* |
| *Y. enterocolitica* | 6 | 1309/80* |
| *E. coli* | 7 | C600/pYET6* |
| *A. tumefaciens* | 8 | C58C1 (rifR)/RP4 (kanR,tetR,carbR)* |
| *A. tumefaciens* | 9 | C58C1 (rifR)/RP4 (kanR,tetR,carbR)* |
| *E. cloacae* | 10 | tks461* |
| *P. aeruginosa* | 11 | IATS* |
| *S. typhimurium* | 12 | ATCC 13311* |
| *Staphylococcus aureus* | 13 | ATCC 25923* |
| *Moraxella catarrhalis* | 14 | 035E* |
| *Y. enterocolitica* | 15 | 20373/79* |
| *Y. intermedia* | 16 | 9/85* |
| *Y. frederikseni* | 17 | 38/83* |
| *Y. frederikseni* | 18 | 3317/84* |
| *Y. kristenseni* | 19 | 119/84* |
| *Y. kristenseni* | 20 | 317/82* |
| *Bacillus cereus* | E1 | ELMI 21# |
| *Bacillus cereus* | E2 | ELMI 170# |
| *Bacillus cereus* | E3 | ELMI 349# |
| *Bacillus cereus* | E4 | ELMI 466# |
| *Bacillus thuriengis* | E5 | ELMI 123# |
| *Bacilus mycoides* | E6 | ELMI 44# |
| *Bacillus licheniformis* | E7 | ELMI 325# |
| *Clostridium difficile* | E8 | ETA/an TYYP 630# |
| *Clostridium perfringens* | E9 | ETA/an 1111# |
| *Clostridium perfringens* | E10 | ETA/an 1701# |
| *Clostridium perfringens* | E11 | ETA/an 1702# |
| *Clostridium septicum* | E12 | ETA/an 1236# |
| *Clostridium sordellii* | E13 | ETA/an 1277# |
| *Fusobacterium necrophorum* | E14 | ETA/an 1318# |
| *Fusobacterium necrophorum* | E15 | ETA/an 1658# |
| *Campylobacter jejuni* | E16 | E1 2702/1/04# |
| *Campylobacter jejuni* | E17 | E1 4966/1/04# |
| *Campylobacter jejuni* | E18 | E1 893/1/03# |
| *Acidobacterium capsulatum* | 34 | DSM 11244 |
| *Deinococcus geothermalis* | 35 | DSM 11300 |
| *Microbacterium barkeri* | 36 | DSM 20145 |
| *Flavobacterium aquatile* | 37 | DSM 1132 |
| *Verromicrobium spinosum* | 38 | DSM 4136 |
| *Planctomyces maris* | 39 | DSM 8797 |
| *Borrelia burgdorferi* | 40 | DSM 4680 |
| *Burkholderia multivorans* | 41 | DSM 13243 |
| *Francisella philomiragia* | 42 | DSM 7535 |
| *F.tularensis* | 21-30 | Clinical sample cultivation |

* The samples were derived from the collection of Mikael Skurnik

§ The samples were derived from the collection of Hiroshi Fukushima, Inst. Pasteur \# The samples were derived from the collection of Vesa Myllys

SEQUENCE LISTING

```
<160> NUMBER OF SEQ ID NOS: 24

<210> SEQ ID NO 1
<211> LENGTH: 19
<212> TYPE: DNA
<213> ORGANISM: Bacillus anthracis

<400> SEQUENCE: 1

cggatagcgg cggttaatc                                               19


<210> SEQ ID NO 2
<211> LENGTH: 26
<212> TYPE: DNA
```

-continued

<213> ORGANISM: Bacillus anthracis

<400> SEQUENCE: 2
caaatgctat tttaagggct tctttt 26

<210> SEQ ID NO 3
<211> LENGTH: 22
<212> TYPE: DNA
<213> ORGANISM: Bacillus anthracis

<400> SEQUENCE: 3
tagaaacgac taaaccggat at 22

<210> SEQ ID NO 4
<211> LENGTH: 21
<212> TYPE: DNA
<213> ORGANISM: Bacillus anthracis

<400> SEQUENCE: 4
ttgggaacgt gtggatgatt t 21

<210> SEQ ID NO 5
<211> LENGTH: 20
<212> TYPE: DNA
<213> ORGANISM: Bacillus anthracis

<400> SEQUENCE: 5
tcagggcggc aattcataat 20

<210> SEQ ID NO 6
<211> LENGTH: 21
<212> TYPE: DNA
<213> ORGANISM: Bacillus anthracis

<400> SEQUENCE: 6
tagtaatcta gctccaattg t 21

<210> SEQ ID NO 7
<211> LENGTH: 23
<212> TYPE: DNA
<213> ORGANISM: Yersinia pestis

<400> SEQUENCE: 7
gaaaggagtg cgggtaatag gtt 23

<210> SEQ ID NO 8
<211> LENGTH: 24
<212> TYPE: DNA
<213> ORGANISM: Yersinia pestis

<400> SEQUENCE: 8
cctgcaagtc caatatatgg cata 24

<210> SEQ ID NO 9
<211> LENGTH: 15
<212> TYPE: DNA
<213> ORGANISM: Yersinia pestis

<400> SEQUENCE: 9
taaccagcgc ttttc 15

<210> SEQ ID NO 10
<211> LENGTH: 28
<212> TYPE: DNA

```
<213> ORGANISM: Francisella tularensis

<400> SEQUENCE: 10

tgagatgata acaagacaac aggtaaca                                          28


<210> SEQ ID NO 11
<211> LENGTH: 27
<212> TYPE: DNA
<213> ORGANISM: Francisella tularensis

<400> SEQUENCE: 11

ggatgagatc ctatacatgc agtagga                                           27


<210> SEQ ID NO 12
<211> LENGTH: 18
<212> TYPE: DNA
<213> ORGANISM: Francisella tularensis

<400> SEQUENCE: 12

ccattcatgt gagaactg                                                     18


<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13

attagaattc gtgaagtgtt accgcaaatt c                                      31


<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14

attaggtacc cggttatgtc tttcccttga t                                      31


<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15

attaggtacc ggatatcagg aaacacgttt c                                      31


<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16

attaggatcc tgtgcccgaa cccagtcg                                          28


<210> SEQ ID NO 17
<211> LENGTH: 31
<212> TYPE: DNA
<213> ORGANISM: Artificial Sequence
<220> FEATURE:
```

-continued

<223> OTHER INFORMATION: Primer

<400> SEQUENCE: 17
attaggatcc ttcgtaaatg gttttgcagc g 31

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
attatctaga cagtcgtttc tccaatcgca 30

<210> SEQ ID NO 19
<211> LENGTH: 30
<212> TYPE: DNA
<213> ORGANISM: Artificial sequence
<220> FEATURE:
<223> OTHER INFORMATION: Primer

<400> SEQUENCE: 19
attatctaga ggagaatgat tatgagtgag 30

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
attactgcag ccgaatcagc tttcgtgac 29

<210> SEQ ID NO 21
<211> LENGTH: 213
<212> TYPE: DNA
<213> ORGANISM: Bacillus anthracis

<400> SEQUENCE: 21
gtgaagtgtt accgcaaatt caagaaacaa ctgcacgtat catttttaat ggaaaagatt 60
taaatctggt agaaaggcgg atagcggcgg ttaatcctag tgatccatta gaaacgacta 120
aaccggatat gacattaaaa gaagccctta aaatagcatt tggatttaac gaaccgaatg 180
gaaacttaca atatcaaggg aaagacataa ccg 213

<210> SEQ ID NO 22
<211> LENGTH: 202
<212> TYPE: DNA
<213> ORGANISM: Bacillus anthracis

<400> SEQUENCE: 22
ttcgtaaatg gttttgcagc gaatgatccc tcatcaacat tacgtatttg ggaacgtgtg 60
gatgattttg gatatagtaa tctagctcca attgtaatta tgaattgccg ccctgaccgc 120
gttgatcgta ctgagcagtt tgctagggat gttttgccat atattaaagc ggaaatagtt 180
attgcgattg gagaaacgac tg 202

<210> SEQ ID NO 23
<211> LENGTH: 212
<212> TYPE: DNA
<213> ORGANISM: Yersinia pestis -continued

<400> SEQUENCE: 23

```
ggatatcagg aaacacgttt cagttggaca gctacaggtg gttcatatag ttataataat     60

ggagcttata ccggaaactt cccgaaagga gtgcgggtaa taggttataa ccagcgcttt    120

tctatgccat atattggact tgcaggccag tatcgcatta atgattttga gttaaatgca    180

ttatttaaat tcagcgactg ggttcgggca ca                                  212
```

<210> SEQ ID NO 24
<211> LENGTH: 204
<212> TYPE: DNA
<213> ORGANISM: Francisella tularensis

<400> SEQUENCE: 24

```
ggagaatgat tatgagtgag atgataacaa gacaacaggt aacaagtggc gagaccattc     60

atgtgagaac tgatcctact gcatgtatag gatctcatcc taattgtaga ttatttattg    120

attctttaac tatagctggg gagaaacttg ataaaaatat cgttgctata gagggtggag    180

aggatgtcac gaaagctgat tcgg                                           204
```

DIAGNOSTIC METHOD AND PRODUCTS USEFUL THEREIN

FIELD OF THE INVENTION

The present invention relates to a method and means useful therein for a simultaneous detection and identification of bacterial species that would likely be used as bioterrorism agents. More particularly, the present invention relates to the simultaneous detection of the presence or absence of *Bacillus anthracis, Yersinia pestis* and *Francisella tularensis* in a single real time PCR assay. The invention also relates to species-specific primers and Taqman MGB probes useful in the method of the invention. The invention further relates to a kit for use in the diagnosis of bacterial bioterrorism agents. In addition, the invention further relates to an infection-free control plasmid to verify the result of the real time PCR analysis method of the invention.

BACKGROUND OF THE INVENTION

The Centres for Disease Control and Prevention (CDC) in United States classifies the biological agents that can possibly be used in a bioterrorist attack into three categories: A, B and C. According to the CDC, category A organisms are considered to pose the greatest risk to public safety. Category A organisms spread easily and the prevention of these agents requires rapid action. Furthermore, the protection against these agents requires large investments from the public health care. Category A agents consist of several viruses and three bacterial species: *B. anthracis, Y. pestis* and *F. tularensis*, which are the causative agents of anthrax, plague and tularemia, respectively.

The use of biological weapons does not necessarily appear instantly, since the incubation time of the organisms in the recipients can be several days, even weeks. It is important to develop diagnostic methods that allow a rapid diagnosis, because after the onset of clinical symptoms the clinical response to antimicrobial treatment is significantly reduced. Therefore, rapid and effective detection of exposure to these pathogens is essential for the initiation of prophylactic treatment before the onset of symptoms. In addition to antimicrobial treatment, prophylactic treatment includes e.g. immunization with vaccines.

The conventional methods for the detection of *B. anthracis, Y. pestis* and *F. tularensis* include the use of microbiological cultures and enzymatic, chemical and immunological assays. The classical microbiological diagnostic methods are often time-consuming and the cultivations can take several days. The need of additional enrichment tests may additionally slow down the procedure, as the pathogens must be distinguished from other, closely related species. Furthermore, the cultivation and enrichment of bacterial species may pose a health risk for laboratory personnel working in, e.g., a deployable field laboratory. Thus, rapid and accurate assays using molecular amplification technologies for the microbiological detection and identification of *B. anthracis, Y. pestis* and *F. tularensis* are essential to ensure proper medical intervention in the case of a suspected intentional release.

The most suitable microbiological tests for diagnosis of anthrax have been designed for blood culture, lumbar puncture or abscesses, in which case the samples are cultured for 1 day and subsequently further identified. In addition, fluorescent-antibody assays are available for rapid detection of anthrax and a result can be obtained in few hours. However, the result needs to be confirmed with alternative methods like PCR, because the specificity of these assays is not 100% reliable. WO 2004070001 discloses a hybridization based method for detecting *B. anthracis* nucleic acid in a sample. The method is based on two detection probes specific for genetic material contained on the pXO1 and pXO2 plasmids. The test is specific and reliable, however the hybridization technique used sets certain requirements for the laboratory work, especially if bacterial strains need to be cultured under the field conditions. Furthermore the analysis is time consuming.

Traditional methods for the identification of plague have several drawbacks. *Y. pestis* grows on general nutrient-rich media, but its growth rate is slower than that of most other bacteria. Therefore its presence may be masked by organisms that replicate faster. Furthermore, the characteristic bipolar staining of *Y. pestis* cells is not an exclusive feature limited to *Y. pestis. Yersinia* spp., enteric bacteria, and other gram-negative organisms, particularly *Pasteurella* spp., can exhibit the same characteristics in staining. Immunological tests for the diagnosis of *Y. pestis* may exhibit cross-reactivity, and therefore are not fully reliable.

*F. tularensis* may be identified by direct examination of secretions, exudates, or biopsy specimens using direct fluorescent antibody or immunohistochemical stains. *F. tularensis* demands a strict growth environment, thus making it hard to cultivate. *F. tularensis* is also one of the most infective bacteria known to man and the handling of infected samples presents an unnecessary risk to the personnel and Biosafety level 3 work protocols are advised. Antigen detection assays, PCR and enzyme-linked immunosorbent assay (ELISA) may be used to identify *F. tularensis*. Serum antibody titres do not attain diagnostic level until 10-14 days after onset of the illness. Therefore, serologic testing is only useful retrospectively: for definitive laboratory confirmation of the disease blood culture and increase in specific antibodies in paired sera are required. Accordingly, rapid identification of *F. tularensis* cannot be achieved with the presently available methods.

Polymerase chain reaction (PCR) analyses have been developed as alternatives for the classical microbiological methods. The traditional PCR is based on end-point analytics, wherein the amplified genetic material can only be inspected with a gel electrophoresis apparatus after the PCR reaction. A series of positive and negative PCR controls is needed to ensure the result and to eliminate the possibility of contamination during the PCR process.

A real-time PCR analysis with specific probes and primers designed for the target gene enables the detection of the PCR reactions already during the reaction. The real-time PCR offers several advantages for the analysis of biological agents that may be used in a bioterrorist attack. First, the real-time PCR is rapid, which is of primary importance in the case of both unintentional and deliberate release of such biological agents. Second, the realtime PCR suits for sensitive and specific pathogen detection, because it is performed in hermetically sealed wells, which greatly reduces the risk of cross-contamination, thereby diminishing the chance of false positive results. Third, the real-time PCR does not require post-PCR analysis.

Several studies disclose the use of a real-time PCR assay for the analysis of isolated bacterial organisms that can be used in a bioterrorist attack. Chase C. J. et al., 2005, Clin Chem 51 (10): 1778-1785, describe real time PCR assays targeting a unique chromosomal sequence of *Y. pestis*. The study indicates that by a real-time PCR assay it is possible to distinguish *Y. pestis* from other *Yersinia* species and from the closely related *Y. pseudotuberculosis*. Bell C. A. et al., 2002, J Clin Microbiol 40:2897-2902, discloses a rapid-cycle real-time PCR detection assay utilizing the LightCycler instrument (Roche Applied Science, Indianapolis) for cultured isolates of *B. anthracis*. Emanuel P. A. et al., 2003, J Clin Microbiol 41:689-693, disclose the detection of *F. tularensis* within infected mouse tissues by using a hand-held thermocycler and compare that to a real-time PCR analysis of tissue samples. However, none of these publications disclose a simultaneous detection of more than one pathogen species using a real-time PCR based method.

In spite of the recognized and obvious advantages of a simultaneous analysis of more than one bacterial pathogen that could be used as bioterrorism agents, no such analysis that would be specific and sensitive enough has so far been developed.

Varma Basil et al., 2004, Clin Chem 50 (6): 1060-1063, describe a real-time PCR assay that simultaneously detects four bacterial agents that could be used in bioterrorism. This study is based on molecular beacons that bind to amplicons generated from *F. tularensis, Burkholderia mallei, Y. pestis* and *B. anthracis*. The analysis takes advantage of 16S rRNA gene sequences, which are highly conserved among bacteria. With the described assay a simultaneous detection of the four pathogens was possible. However, the *Y. pestis* assay used cross-reacted strongly with 4 control bacterial species present in the samples. Such an assay would not be acceptable, since false-positive results in the diagnosis of category A agents would lead to significant economical losses and compromise the trust of the general public to the authorities.

Since the detection of Category A agents has to be absolutely accurate, rapid and reliable, further methods for efficient microbial detection of category A agents are still needed.

BRIEF DESCRIPTION OF THE INVENTION

To overcome the drawbacks of the prior art assays, a new approach was developed. While the real-time PCR assay described by Varma Basil et al., supra, utilizes conserved 16S rRNA gene sequences and molecular beacons, the present invention takes advantage of species-specific gene or plasmid sequences and the optimization of the concentrations of the primers and probes derived from these species-specific gene or plasmid sequences to provide a highly sensitive PCR reaction using identical temperature parameters. Such a PCR reaction allows a simultaneous detection of bacterial category A pathogens which could be used as bioweapons or bioterrorism agents.

Accordingly, an object of the present invention is to provide novel methods and means for a simultaneous detection and identification of bacterial species that would likely be used as bioterrorism agents.

Another object of the invention is to provide novel methods and means, by which it is possible to detect and identify simultaneously bacterial species that would likely be used as bioterrorism agents, substantially more rapidly than has been previously possible, whereby correct and effective anti-microbial therapy or prophylaxis to the affected subjects and, as importantly, the necessary measures to prevent further spreading of the disease and the agents can be initiated at an earlier stage than before.

A further object of the invention is to provide means and methods that are useful in detection and identification of bacterial species that would likely be used as bioterrorism agents, the means and methods being reliable, sensitive, and being capable of identifying specifically only the desired bacterial species.

The present invention relates to a method for simultaneously detecting the presence or absence of bacterial species *Bacillus anthracis, Yersinia pestis* and *Francisella tularensis* in a single real time PCR assay run using Taqman MGB probes and species-specific primers, wherein a) the forward and reverse primers for *B. anthracis* have the sequences of SEQ ID NOS: 1 and 2, respectively, derived from the pagA gene and SEQ ID NOS: 4 and 5, respectively, derived from the capB gene, b) the forward and reverse primers for *Y. pestis* have the sequences of SEQ ID NOS: 7 and 8, respectively, derived from the pla gene, and c) the forward and reverse primers for *F. tularensis* have the sequences of SEQ ID NOS: 10 and 11, respectively, derived from the 23 kDa gene, and wherein the concentrations of said forward primers and said reverse primers are optimized in the range of 50-900 nM under the same temperature parameters.

The specific Taqman MGB probes used in the method of the invention are for *B. anthracis* the sequence of SEQ ID NO: 3 derived from the pagA gene and the sequence of SEQ ID NO: 6 derived from the capB gene, for *Y. pestis* the sequence of SEQ ID NO: 9 derived from the pla gene, and for *F. tularensis* the sequence of SEQ ID NO: 12 derived from the 23 kDa gene.

In one embodiment of the method of the invention a multiplex PCR-format is used, wherein the reactions are performed in a single assay tube using differently labelled Taqman MGB probes.

The present invention also relates to novel species-specific primers useful in the method of the invention, said species-specific primers having the sequences of SEQ ID NOS: 1 and 2 derived from the *Bacillus anthracis* pagA gene, SEQ ID NOS: 4 and 5 derived from the *B. anthracis* capB gene, SEQ ID NOS: 7 and 8 derived from the *Yersinia pestis* pla gene, and SEQ ID NOS: 10 and 11 derived from the *Francisella tularensis* 23 kDa gene, and to their use in PCR based assays for the detection of *B. anthracis, Y. pestis* and *F. tularensis*, respectively.

The present invention further relates to novel Taqman MGB probes useful in the method of the invention, said Taqman MGB probes having the sequences of SEQ ID NO: 3 derived from the *Bacillus anthracis* pagA gene, SEQ ID NO: 6 derived from the *B. anthracis* capB gene, SEQ ID NO: 9 derived from the *Yersinia pestis* pla gene, and SEQ ID NO: 12 derived from the *Fransisella tularensis* 23 kDa gene, and to their use in PCR based assays.

The present invention further relates to a diagnostic kit for use in the diagnosis of bacterial species that would likely be used as bioterrorism agents, comprising a) species-specific primers of the invention as defined above, b) specific Taqman MGB probes of the invention as defined above, and optionally, c) internal positive controls and reagents required in the amplification, hybridisation, purification washing, and/or detection steps.

The present invention also relates to an infection risk-free control plasmid comprising partial sequences of the *Bacillus anthracis* pagA and capB genes having the sequences of SEQ ID NOS: 21 and 22, respectively, the *Yersinia pestis* pla gene having the sequence of SEQ ID NO: 23, and the *Francisella tularensis* 23 kDa gene having the sequence of SEQ ID NO: 24 and the appropriate promoter and regulatory sequences.

DESCRIPTION OF THE DRAWINGS

FIG. 1 shows the bacterial organisms used to test the specificity of the method of the invention.

DETAILED DESCRIPTION OF THE INVENTION

Figure 2:
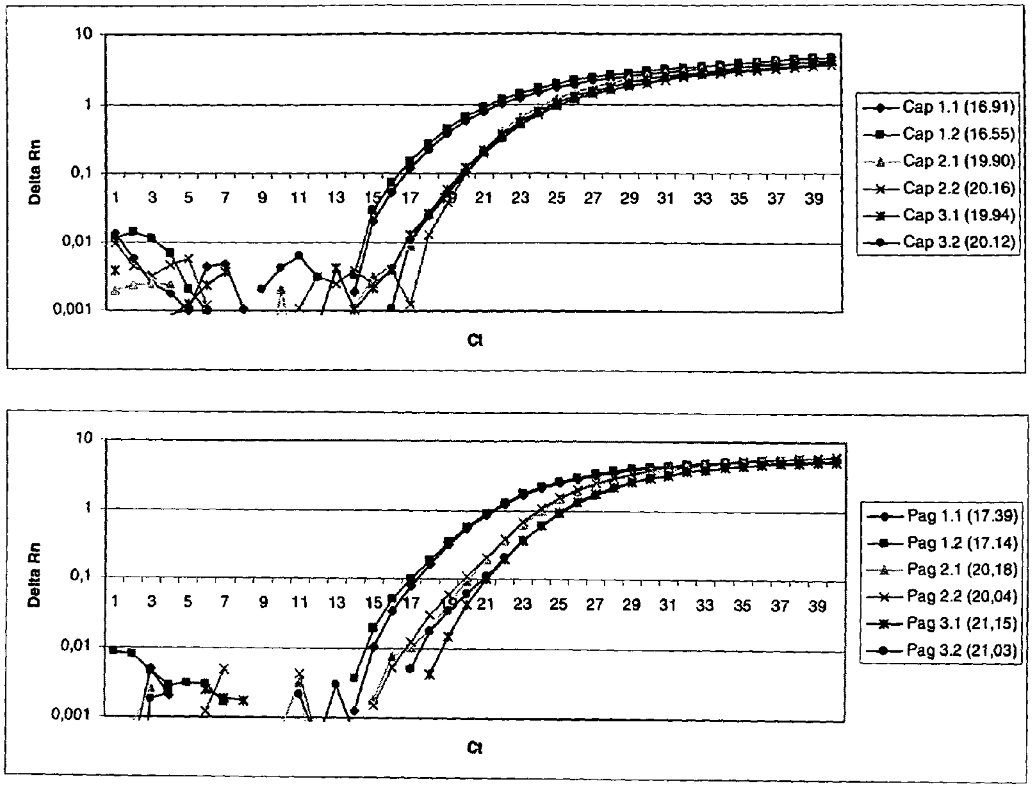
FIG. 2 shows a real time PCR analysis of a tissue sample from an infected cow using ABI 7300 Taqman-MGB assay targeting plasmids pXO1 (pagA) and pXO2 (capB) of *B. anthracis*. Three separate isolations (1, 2, and 3) were run in duplicates. Ct values are shown on the right.

The present invention is based on studies, which attempted to find more rapid and specific alternatives for the detection and diagnosis of biological agents that could be used in a bioterrorist attack. It was unexpectedly found that more than one of the category A bacterial species can be amplified and detected simultaneously in a specific and reliable manner using the real-time PCR techniques. This was achieved by designing novel real time PCR primers and probes for *B. anthracis, Y. pestis* and *F. tularensis* bacteria and adjusting the operating conditions for these species-specific primer and probe sequences so that all have similar melting temperatures in the presence of perfectly complementary targets.

Specifically the present invention relates to a method for the simultaneous detection of the presence or absence of bacterial species *Bacillus anthracis, Yersinia pestis* and *Francisella tularensis* in a single real time PCR assay run using Taqman MGB probes and species-specific primers, wherein a) the forward and reverse primers for *B. anthracis* have the sequences of SEQ ID NOS: 1 and 2, respectively, derived from the pagA gene and SEQ ID NOS: 4 and 5, respectively, derived from the capB gene, b) the forward and reverse primers for *Y. pestis* have the sequences of SEQ ID NOS: 7 and 8, respectively, derived from the pla gene, and c) the forward and reverse primers for *F. tularensis* have the sequences of SEQ ID NOS: 10 and 11, respectively, derived from the 23 kDa gene, and wherein the concentrations of said forward primers and said reverse primers are optimized in the range of 50-900 nM under the same temperature parameters.

The specific Taqman MGB probes used in the method of the invention have the sequences of SEQ ID NO: 3 derived from the *B. anthracis* pagA gene, SEQ ID NO: 6 derived from the *B. anthracis* capB gene, SEQ ID NO: 9 derived from the *Y. pestis* pla gene, and SEQ ID NO: 12 derived from the *F. tularensis* 23 kDa gene.

For the present purposes the expression “simultaneously detecting” means that a single real time PCR assay run is performed simultaneously for each bacteria either in separate reaction vessels, such as wells or tubes, or in a single reaction vessel with species-specific primers and Taqman MGB probes. Preferably the run is performed in separate reaction vessels. However, in one embodiment of the method of the invention a multiplex PCR-format is used, wherein the reactions are performed in a single assay tube using differently labelled Taqman MGB probes.

The present invention also relates to novel species-specific primers useful in the method of the invention, said species-specific primers having the sequences of SEQ ID NOS: 1 and 2 derived from the *Bacillus anthracis* pagA gene, the sequences of SEQ ID NOS: 4 and 5 derived from the *B. anthracis* capB gene, the sequences of SEQ ID NOS: 7 and 8 derived from the *Yersinia pestis* pla gene, and the sequences of SEQ ID NOS: 10 and 11 derived from the *Francisella tularensis* 23 kDa gene, and to their use in PCR based assays.

The present invention further relates to novel Taqman MGB probes that are utilized in the method of the invention, said Taqman MGB probes having the sequences of SEQ ID NO: 3 derived from the *Bacillus anthracis* pagA gene, SEQ ID NO: 6 derived from the *B. anthracis* capB gene, SEQ ID NO: 9 derived from the *Yersinia pestis* pla gene, or SEQ ID NO: 12 derived from the *Francisella tularensis* 23 kDa gene, and to their use in PCR based assays.

The present invention further relates to a diagnostic kit for use in the diagnosis of bacterial species that would likely be used as bioterrorism agents, comprising a) species-specific primers for *Bacillus anthracis, Yersinia pestis* and *Francisella tularensis*, wherein the forward and reverse primers for *B. anthracis* have the sequences of SEQ ID NOS: 1 and 2 derived from the pagA gene and SEQ ID NOS: 4 and 5 derived from the capB gene, the forward and reverse primers for *Y. pestis* have the sequences of SEQ ID NOS: 7 and 8 derived from the pla gene and the forward and reverse primers for *F. tularensis* have the sequences of SEQ ID NOS: 10 and 11 derived from the 23 kDa gene, b) specific Taqman MGB probes for *B. anthracis, Y. pestis* and *F. tularensis*, said Taqman MGB probe having the sequence of SEQ ID NO: 3 derived from the *B. anthracis* pagA gene, the sequence of SEQ ID NO: 6 derived from the *B. anthracis* capB gene, the sequence of SEQ ID NO: 9 derived from the *Y. pestis* pla gene, or the sequence of SEQ ID NO: 12 derived from the *F. tularensis* 23 kDa gene, and to their use in PCR based assays, and optionally c) internal positive controls and reagents required in the amplification, hybridisation, purification, washing, and/or detection steps.

The present invention also relates to an infection risk-free control plasmid comprising partial sequences of *Bacillus anthracis* pagA and capB genes having the sequences of SEQ ID NOS: 21 and 22, respectively, *Yersinia pestis* pla gene having the sequence of SEQ ID NO: 23, and *Francisella tularensis* 23 kDa gene having the sequence of SEQ ID NO: 24 and the appropriate promoter and regulatory sequences.

The primers and MGB probes of the present invention were designed so as to make the selected nucleic acid sequences as species-specific as possible and to make them attach only to the corresponding DNA sequences of their target organisms. In the design of primers and probes the Primer Express ver. 2.0 software (Applied Biosystems, CA, USA) was used. The designed primer/Taqman MGB probe combinations were based on sequences available from the NCBI public database.

In the design of novel primers and probes of the present invention the following criteria were used: predicted cross-reactivity with currently available GenBank sequences, lack of primer-dimer formation, self-annealing of nucleotide, a +10° C. higher melting temperature of the probe than the primers, no stretches of identical nucleotides more than four, and no guanine at the 5' end of the probe. Additionally, to prevent and minimize the possibility of non-specificity caused by mutations in the target genes, the size of the target sequences had to be as short as possible. The primers and probes of the invention were synthesized by Applied Biosystems (Cheshire, England).

Specifically, for designing the *B. anthracis* specific forward primers (pagF and capF; SEQ ID NO: 1 and SEQ ID NO: 4, respectively) and reverse primers (pagR and capR; SEQ ID NO: 2 and SEQ ID NO: 5, respectively) and Taqman MGB probes (pagR and capR; SEQ ID NO: 3 and SEQ ID NO: 6, respectively) the pagA gene (GenBank accession no. M22589) and the capB gene (GenBank accession no. M24150) of *B. anthracis* virulence plasmids pXO1 and pXO2, respectively, were used. The pagA gene of plasmid pXO1 encodes for a protective antigen, which is one of the three genes encoding the *B. anthracis* toxin complex. The capB gene is one of the three genes on plasmid pXO2 that are necessary for biosynthesis of the protective polypeptide capsule (Hanna, P., 1988, Curr. Top. Microbiol. Immunol. 225: 13-35). On the basis of design criteria nucleotides 3400 to 3488 of the pagA coding sequence and nucleotides 1106 to 1174 of the capB coding sequence provided the most sensitive target for the assay. Since plasmids pXO1 and pXO2 must both be present for a *B. anthracis* isolate to be virulent, both pagA and capB genes were included in the assay. Apathogenic *B. anthracis* strains lacking either one or both plasmids have been isolated from the environment. The detection sites of the capB and pagA genes were designed to be only 68 and 84 base pairs, respectively, in length, thus reducing the probability of mutations.

*Y. pestis* specific primers (plaF, plaR) were subjected to target plasminogen activator gene pla (GenBank accession no. M27820) of *Y. pestis* virulence plasmid pCP1. The plasminogen activator gene has been found to be the most sensitive target, since its copy number can be high as 186 per bacterium (Loiez C. et al., 2003, J Clin Microbiol 41: 4873-4875). The reverse primer (plaR; SEQ ID NO: 8) and the Taqman MGB probe (plaTM; SEQ ID NO: 9) were specifically designed. The forward primer (plaF; SEQ ID. NO: 7) was as described by Loiez C. et al., supra. The amplification target for the pla gene was designed to be only 62 base pairs in length, which makes it highly species-specific and reduces the probability of mutations.

The *F. tularensis* primers and probe target the 23 kDa gene (GenBank accession no. Y08861), which is an important factor in the intracellular growth of *F. tularensis* on macrophages. The Taqman MGB-probe (23 kDaTM; SEQ ID NO: 12) was specifically designed, but since the 23 kDa gene has successfully been used for detection in real time Taqman PCR-assay, known primers (23F and 23R; SEQ ID NOS: 10 and 11) could be used (Versage, J. L., et al., 2003, J Clin Microbiol 41:5492-5499). Again, the amplification target for the 23 kDa gene was short, only 83 base pairs.

In general and as used in the present invention the term "TaqMan probe" refers to oligonucleotides that contain a fluorescent dye, typically on the 5' base, and a nonfluorescent quenching dye (quencher), typically on the 3' base. When irradiated, the excited fluorescent dye transfers energy to the nearby quenching dye molecule rather than fluorescing, resulting in a non-fluorescent substrate. The term "TaqMan MGB probe" refers to a TaqMan probe conjugated with a minor groove binder (MGB) at the 3'-end of the probe. MGB is tripeptide 1,2-dihydro-(3H)-pyrrolo[3,2-e]indole-7-carboxylate (CDPI3) which binds to the minor groove of DNA with high affinity. Stabilizing van der Waals forces increase the melting temperature (Tm) of MGB probes without increasing probe length and thus enable the use of shorter probes than in normal Taqman real-time PCR. Additionally, the background fluorescence is quenched more efficiently by using the MGB-probes. In the present invention TaqMan MGB probes (Applied Biosystems) were used. The species-specific sequences of the designed probes were 15 to 21 nucleotides in length.

The primers and probes used in the present invention are shown in Table 1.

TABLE 1

PRIMERS AND PROBES

| Primers and probes | Primer sequence | Primer position* | Fragment size (bp) | SEQ ID NO: |
|---|---|---|---|---|
| pag | | | 84 | |
| pagF | 5'-CGG ATA GCG GCG GTT AAT C -3' | 3400-3418 | | 1 |
| pagR | 5'-CAA ATG CTA TTT TAA GGG CTT CTT TT -3' | 3484-3459 | | 2 |
| pagTM | 5'-TAG AAA CGA CTA AAC CGG ATA T -3' | 3431-3452 | | 3 |
| cap | | | 68 | |
| capF | 5'-TTG GGA ACG TGT GGA TGA TTT -3' | 1106-1126 | | 4 |
| capR | 5'-TCA GGG CGG CAA TTC ATA AT-3' | 1174-1155 | | 5 |
| capTM | 5'-TAG TAA TCT AGC TCC AAT TGT -3' | 1133-1153 | | 6 |
| pla | | | 62 | |
| plaF | 5'-GAA AGG AGT GCG GGT AAT AGG TT -3' | 816-838 | | 7 |
| plaR | 5'-CCT GCA AGT CCA ATA TAT GGC ATA -3' | 878-855 | | 8 |
| plaTM | 5'-TAA CCA GCG CTT TTC -3' | 840-854 | | 9 |
| 23 kDa | | | 83 | |
| 23F | 5'-TGA GAT GAT AAC AAG ACA ACA GGT AAC A -3' | 551-578 | | 10 |
| 23R | 5'-GGA TGA GAT CCT ATA CAT GCA GTA GG A -3' | 634-608 | | 11 |
| 23TM | 5'-CCA TTC ATG TGA GAA CTG-3' | 589-606 | | 12 |

*Based on GenBank accession numbers M22589 (pagA), M24150 (capC), M27820 (pla), and Y08861 (23 kDa).

All real-time PCR systems rely upon the detection and quantitation of a fluorescent reporter, the signal of which increases in a direct proportion to the amount of the PCR product that is forming in a reaction. Such reporters can be hybridisation probes relying on fluorescence resonance energy transfer (FRET) for quantification. In the present invention any suitable fluorophores can be used in order to produce a fluorescent Taqman MGB probe. Suitable fluorescent labels include fluorescent labels such as FAM/SYBR Green, VIC/JOE, NED/TAMRA/Cy3, ROX/Texas Red, and Cy5 dyes. In the preferred embodiment of the present invention the fluorescent reporter dye at the 5' end of the probe is 6-carboxy-fluorescein (FAM), and the 3' end the non-fluorescent quencher is the one supplied by Applied Biosystems.

To allow efficient simultaneous detection of *B. anthracis, F. tularensis* and *Y. pestis* using similar thermocycling profiles the concentrations of the primers and probes were optimized. The optimization experiments were based on ABI 7300 instrument manual (Applied Biosystems 7300 Sequence Detection System; Training course manual, chapter 12) and performed as follows. Various concentrations of each of the primers and probes were tested in a matrix format so that concentrations of 50, 300 or 900 nM of reverse primers were tested in combination with concentrations of 50, 300 or 900 nM of forward primers. The probe concentrations were optimized by varying concentrations in the range of 50-250 nM. The optimal concentrations were chosen based on the lowest Ct (earliest cycle threshold) combined with the greatest end point fluorescence. The optimization of the concentrations allows the analysis of the three bacteria simultaneously rather than performing individual assays for each bacteria.

The optimal PCR conditions were for the *B. anthracis* assay 300 nM forward primer and 900 nM reverse primer, for *Y. pestis* assay 50 nM forward primer and 300 nM reverse primer and for *F. tularensis* assay 300 nM forward primer and 900 nM reverse primer. The Taqman MGB probe concentration of 250 nM provided highly reproducible and sensitive assays and thus it was used in all assays.

In the practice of the invention the real-time PCR analysis for the detection and identification of bacteria that cause anthrax, tularemia or plague was performed using ABI 7300 thermocycler (Applied Biosystems, Foster City, Calif., USA). However, as evident to persons skilled in the art, the analysis could be performed on other fluorescence-based thermocyclers, which permit rapid cycling and simultaneous detection of the amplification product provided that the systems used can utilize the present assay reagents.

In the method of the present invention, the sample to be analyzed can be a bacterial culture, a tissue fragment, a secretion sample, such as a sputum or brush sample, a blood sample, a clinical sample from lumbar puncture or abscesses, or another suitable sample, obtained from a patient suspected of suffering of the infectious disease in question. The sample can also be an environmental sample, such as an earth sample, a paper sample or an air sample collected from the site to be examined, or any other environmental sample from which nucleic acid can be isolated.

Because the primer pairs used in the method of the invention are very specific, the analysis only requires small amounts of samples, and could from suitable samples be analysed even without any preceding nucleic acid purification and isolation steps. Preferably, however, DNA is isolated from the sample to be analyzed with any conventional method, such as with commercial DNA isolation kits (e.g., MagNAPure LC System, Roche, High Pure PCR Template Preparation Kit, Roche; NucleoSpin, BD Biosciences Clontech; or QIAamp DNA Mini-kit, Qiagen) or with conventional extraction. Commercial kits are preferably used because of their general availability, rapidity, repeatability and safety.

In the method of the present invention the reagents used in DNA amplification can be any reagents that are conventionally used for the amplification of DNA, and are well known among the persons skilled in the art. Suitable and most easy to use is commercially available Taqman Universal PCR master mix (Applied Biosystems) containing dNUTP'S, MgCl2, reaction buffer, AmpErase® uracil-N-glycosylase (UNG), ROX passive reference and AmpliTaq Gold®. However, also different types of thermostable DNA polymerases and buffers thereto (e.g., AmpliTaqLD, DyNAzyme, TaqPlus Precision, and HotStartTaq), nucleotides or pre-prepared mixtures of nucleotides (e.g., Sigma, Applied Biosystems, Amersham Biosystems), MgCl2 (whereby a product from the manufacturer of the Taq polymerase is generally used) could be used.

A major advantage of the method of the invention is that the detection of bioterrorism agents *B. anthracis, Y. pestis* and *F. tularensis* is very rapid as all three bacteria can be detected simultaneously. Before the present invention a successful detection of these bacteria by real-time PRC had been done in three different analysis runs. Loiez C. et al., supra discloses detection of *Y. pestis* and Versage, J. L. et al., supra discloses detection of *F. tularensis* by real time PCR, however, these methods cannot be used for the simultaneous detection of all three bacteria without the optimization of the PCR conditions as described in the present invention. WO 2005030991 and Charrel, R. N. et al., 2004 BMC Microbiology, 4:21, 1-11, disclose a PCR based method for detecting the presence of a bacterial or viral DNA agent for bioterrorism. According to this method the fragments amplified by PCR from the bacterial DNA locate on *B. anthracis* pagA, *Y. pestis pla, F. tularensis* fopA and variolavirus hemagglutinin genes. In addition, WO 2005030991 does not disclose the use of capB gene for the detection of *B. anthracis*. The method thus allows also detection of avirulent *B. anthracis* strains.

The method of invention is highly sensitive corresponding to 1 bacterial cell with all three Category A agents. The detection of *B. anthracis* is at least as sensitive as known from the prior art (Bell, C. A., et al., 2002, J Clin Microbiol 40:2897-2902; Ellerbrok, H., H. et al., 2002, FEMS Microbiol Lett 214:51-59; Reif, T. C., et al., 1994, Appl Environ Microbiol 60:1622-1625). For the detection of *F. tularensis* the sensitivity of 0.1 genomic equivalents (GE) was achieved. The earlier studies have reported sensitivity of 5 (GE) (Bastien, M., et al., 2005, ASM Biodefence Research Meeting 2005, abstract). The sensitivity for the *Y. pestis* detection was 0.2 GE. The earlier studies have re-ported sensitivity of approx 20 GE (Chase, C. J. et al., 2005, Clin Chem 51:1778-1785).

As importantly, the method of the invention is highly specific, since none of closely related bacterial species are detected.

An additional advantage of the present invention is the rapidity it provides for the diagnosis of category A bacterial bioterrorism agents. An analytical turnaround time of less than 120 minutes post specimen processing is possible with the ABI 7300 96-plate assay of the invention. Extraction of DNA can be accomplished in 30 minutes using commercial kits. All reactions include internal positive controls, which can be used in the assessment of inhibitorial factors in samples thus reducing the time for analysis. The total time for specimen processing and analysis is less than three hours.

The diagnostic kit of the present invention is designed for use in the diagnosis of bacterial species that would likely be used as bioterrorism agents. The kit comprises a) species-specific primers for *B. anthracis, Y pestis* and *F. tularensis*, wherein the forward and reverse primers for *B. anthracis* have the sequences of SEQ ID NOS: 1 and 2 derived from the pagA gene and SEQ ID NOS: 4 and 5 derived from the capB gene, the forward and reverse primers for *Y. pestis* have the sequences of SEQ ID NOS: 7 and 8 derived from the pla gene and the forward and reverse primers for *F. tularensis* have the sequences of SEQ ID NOS: 10 and 11 derived from the 23 kDa gene, b) specific Taqman MGB probes for *B. anthracis, Y. pestis* and *F. tularensis*, said Taqman MGB probes having the sequence of SEQ ID NO: 3 derived from the *B. anthracis* pagA gene, the sequence of SEQ ID NO: 6 derived from the *B. anthracis* capB gene, the sequence of SEQ ID NO: 9 derived from the *Y. pestis* pla gene, or the sequences of SEQ ID NO: 12 derived from the *F. tularensis* 23 kDa gene, and to their use in PCR based assays, and optionally c) internal positive controls and reagents required in the amplification, hybridisation, purification, washing, and/or detection steps.

To verify the positive result of the real time PCR analysis method of the invention an infection risk-free control plasmid can be constructed. The control plasmid comprises partial sequences of the *B. anthracis* pagA and capB genes having the sequences of SEQ ID NOS: 21 and 22, respectively, the *Y. pestis* pla gene having the sequence of SEQ ID NO: 23, and the *F. tularensis* 23 kDa gene having the sequence of SEQ ID NO: 24 (Table 3) and the appropriate promoter, replication and regulatory sequences. The gene regions of the *B. anthracis* pagA and capB genes, the *Y. pestis* pla gene and the *F. tularensis* 23 kDa gene are amplified in a traditional PCR using primers that include sites for the restrictions enzymes as shown in Table 2. The amplified gene regions are separately cloned to the *E. coli* vector pUC19 multiple cloning sites. Subsequently, the four different plasmids are combined by restriction and ligation reactions resulting in a non-infectious plasmid, which contains all four gene regions. The plasmid can thus be used as a positive control for all the primers of the invention.

A major advantage of the infection risk-free control plasmid of the invention is that by using this plasmid the verification of the PCR results of bioterrorism agents *B. anthracis, Y. pestis* and *F. tularensis* is very specific and more sensitive in comparison to the control plasmids of the prior art (WO 2005030991 and Charrel, R. N. et al., 2004 BMC Microbiology, 4:21, 1-11).

TABLE 2

RESTRICTION PRIMERS FOR CONSTRUCTING THE INFECTION-FREE CONTROL PLASMID

| Primers | primer position[a] | fragment size (bp) | SEQ ID NO: |
|---|---|---|---|
| B. anthracis pagA (AC M22589) | | 213 | |
| PagF (EcoRI) | 3323-3343 | | 13 |
| 5' ATTA**<u>GAATTC</u>**GTGAAGTGTTACCGCAAATTC | | | |
| pagR (Kpnl) | 3535-3515 | | 14 |
| 5' ATTA**<u>GGTACC</u>**CGGTTATGTCTTTCCCTTGAT | | | |
| Y. pestis pla (AC M27820) | | 212 | |
| plaF (Kpnl) | 733-753 | | 15 |
| 5' ATTA**<u>GGTACC</u>**GGATATCAGGAAACACGTTTC | | | |
| plaR (BamHI) | 944-927 | | 16 |
| 5' ATTA**<u>GGATCC</u>**TGTGCCCGAACCCAGTCG | | | |
| B. anthracis capB (AC M24150) | | 202 | |
| capF (BamHl) | 1059-1079 | | 17 |
| 5' ATTA**<u>GGATCC</u>**TTCGTAAATGGTTTTGCAGCG | | | |
| capR (Xbal) | 1260-1241 | | 18 |
| 5' ATTA**<u>TCTAGA</u>**CAGTCGTTTCTCCAATCGCA | | | |
| F. tularensis gene encoding 23 kDa protein (AC Y08861) | | 204 | |
| 23F (Xbal) | 535-554 | | 19 |
| 5' ATTA**<u>TCTAGA</u>**GGAGAATGATTATGAGTGAG | | | |
| 23R (Pstl) | 738-720 | | 20 |
| 5' ATTA**<u>CTGCAG</u>**CCGAATCAGCTTTCGTGAC | | | |

TABLE 3

THE PLASMID SEQUENCES IN THE INFECTION-FREE CONTROL PLASMID

| Name | Plasmid sequence | SEQ ID NO: |
|---|---|---|
| PAG | gtgaagtgtt accgcaaatt<br>caagaaacaa ctgcacgtat<br>catttttaat ggaaaagatt<br>taaatctggt agaaaggcgg<br>atagcggcgg ttaatcctag<br>tgatccatta gaaacgacta<br>aaccggatat gacattaaaa<br>gaagccctta aaatagcatt<br>tggatttaac gaaccgaatg<br>gaaacttaca atatcaaggg<br>aaagacataa ccg | 21 |
| CAP | ttcgtaaatg gttttgcagc<br>gaatgatccc tcatcaacat<br>tacgtatttg ggaacgtgtg<br>gatgattttg gatatagtaa<br>tctagctcca attgtaatta<br>tgaattgccg ccctgaccgc<br>gttgatcgta ctgagcagtt<br>tgctagggat gttttgccat<br>atattaaagc ggaaatagtt<br>attgcgattg gagaaacgac tg | 22 |
| PLA | ggatatcagg aaacacgttt<br>cagttggaca gctacaggtg<br>gttcatatag ttataataat<br>ggagcttata ccggaaactt | 23 |

TABLE 3-continued

THE PLASMID SEQUENCES IN THE INFECTION-FREE CONTROL PLASMID

| Name | Plasmid sequence | SEQ ID NO: |
|---|---|---|
| | cccgaaagga gtgcgggtaa<br>taggttataa ccagcgcttt<br>tctatgccat atattggact<br>tgcaggccag tatcgcatta<br>atgattttga gttaaatgca<br>ttatttaaat tcagcgactg<br>ggttcgggca ca | |
| 23 kDa | ggagaatgat tatgagtgag<br>atgataacaa gacaacaggt<br>aacaagtggc gagaccattc<br>atgtgagaac tgatcctact<br>gcatgtatag gatctcatcc<br>taattgtaga ttatttattg<br>attctttaac tatagctggg<br>gagaaacttg ataaaaatat<br>cgttgctata gagggtggag<br>aggatgtcac gaaagctgat tcgg | 24 |

It will be obvious to a person skilled in the art that, as the technology advances, the inventive concept can be implemented in various ways. The invention and its embodiments are not limited to the examples described below but may vary within the scope of the claims.

EXAMPLES

Example 1

Primer and Probe Selection

The design of primer/Taqman MGB probe combinations was based on the sequences of *B. anthracis, Y. pestis* and *F. tularensis* available from the NCBI public database (http://www.ncbi.nlm.nih.gov/blast/). The primer and probe sequences were selected based on the following criteria: predicted cross-reactivity with currently available GenBank sequences, lack of primer-dimer formation, self annealing of nucleotide, a +10° C. higher melting temperature of the probe than primers, no stretches of identical nucleotides than four, and no guanine at the 5' end of the probe. The design was done using the Primer Express ver. 2.0 software (Applied Biosystems, CA, USA).

The fluorescent reporter dye conjugated at the 5' end of the Taqman MGB probe was a 6-carboxy-fluorescein (FAM) and in the 3' end a non-fluorescent quencher (Applied Biosystems, CA, USA).

*B. anthracis* specific primers pagF (SEQ ID NO: 1), pagR (SEQ ID NO: 2), capF (SEQ ID NO: 4), capR (SEQ ID NO: 5), and Taqman MGB probes pagTM (SEQ ID NO: 3) and capTM (SEQ ID NO: 6) were designed from the pag gene (GenBank accession no. M22589) and from the cap gene (GenBank accession no. M24150) of virulence plasmids pXO1 and pXO2, respectively. *Y. pestis* specific primers plaF (SEQ ID NO: 7) and plaR (SEQ ID NO: 8) were designed to target the pla gene (GenBank accession no. M27820) of virulence plasmid pCP1. The plaF primer was chosen from Loiez et al., 2003, supra, and the plaR primer and Taqman MGB plaTM probe were specifically designed. The *F. tularensis* primers and probe targeted the 23 kDa gene (GenBank accession no. Y08861). Both primers 23F (SEQ ID NO: 10) and 23R (SEQ ID NO: 11) were chosen from (Versage, J. L., et al., 2003, J Clin Microbiol 41:5492-5499), and the Taqman MGB probe, 23 kDaTM (SEQ ID NO: 12), was specifically designed. The primers and probes (Table 1) were synthesized by Applied Biosystems (Cheshire, England).

Example 2

The Real-Time PCR Analysis of Category a Bacterial Agents

For the PCR analysis DNA was isolated from the bacterial strains and isolates listed in FIG. 1. The strains 1-20 and Y1-Y48 were from the collections of Haartman Institute, Division of Bacteriology and Immunology, Helsinki, Finland. Bacterial strains E1-E18 were from the National Veterinary and Food Research Institute, University of Helsinki, Finland. All isolates (1-20 and E1-E18) and positive controls: *B. anthracis* Sterne 7702, *B. anthracis* ATCC 4229, *Y. pestis* EV76-c and *F. tularensis* LVS-strains were grown according to conventional microbiological methods. Strains 34-42 were acquired from DSMZ (Braunschweig, Germany), and grown according to the DSMZ instructions except for *Verromicrobium spinosum, Borrelia burgdorferi* and *F. philomiragia* that were received as actively growing cultures.

All the bacterial isolates were purified using the automated MagNAPure LC System (Basel, Switzerland) according to the manufacturers LC DNA Isolation Kit III manual. The control strains of *B. anthracis, F. tularensis*, and *Y. pestis* were grown overnight and divided into aliquots followed by purification with the QiaAmp DNA miniKit (Qiagen, Hilden, Germany). *Y. pseudotuberculosis* samples were received as purified DNA. Total DNA extracted from the bacterial isolates was measured with the Genequant RNA/DNA calculator (BioChrom Ltd, Cambridge, UK).

A real-time PCR analysis was performed for the isolated DNA samples. The real-time PCR reaction mixture consisted of 2.5 μl DNA sample, 12.5 μl 2× Taqman Universal PCR master mix (Applied Biosystems) containing dNUTP'S, MgCl2, reaction buffer, AmpErase®uracil-N-glycosylase (UNG), ROX passive reference and AmpliTaq Gold®. Additionally, 2.5 μl of IPC mix and 0.5 μl IPC synthetic DNA were used. All assays were run in a final volume of 25 μl.

The concentrations of the primers and probes (Example 1) were optimized. The optimization experiments were based on ABI 7300 instrument manual (Applied Biosystems 7300 Sequence Detection System; Training course manual, chapter 12) and performed as follows. Various concentrations of each of the primers and probes were tested in a matrix format so that concentrations of 50, 300 or 900 nM of reverse primers were tested in combination with concentrations of 50, 300 or 900 nM of forward primers. The concentrations of the probes were optimized by varying concentrations in the range of 50-250 nM. The optimal concentrations were chosen based on the lowest Ct (earliest cycle threshold) combined with the greatest end point fluorescence.

The optimized PCR conditions for the *B. anthracis* assay were the following; 300 nM forward primer, 900 nM reverse primer and 250 nM of fluorescence labelled Taqman probe. *B. anthracis* strains Sterne 7702 (pXO1+/pXO2−) and ATCC 4229 (pXO1−/pXO2+) were used as positive controls. The PCR reactions for *Y. pestis* contained 50 nM forward primer, 300 nM reverse primer and 250 nM of fluorescence labelled Taqman probe. *Y. pestis* strain EV76-c was used as a positive control. In the *F. tularensis* assays 300 nM forward primer, 900 nM reverse primer and 250 nM of fluorescence labelled Taqman probe were used. *F. tularensis* LVS-strain was used as a positive control. The following control reactions were included in all diagnostic runs: in the No Amplification Controls (NAC) the template was substituted with Internal Positive Control (IPC) Blocker, and in No Template Controls (NTC) with water. Both controls were replicated six times.

The real-time PCR analysis was performed simultaneously for *B. anthracis, Y. pestis* and *F. tularensis* in a 96-plate assay with the ABI 7300 thermocycler (Applied Biosystems) using the following parameters: 2 min at 50° C., 10 min at 95° C., 40 cycles of 15 s at 95° C. and 1 min at 60° C. The obtained fluorescence data was analyzed with the Sequence Detector software (Applied Biosystems).

Example 3

The Sensitivity and Specificity of the Method of Invention

In order to determinate the range of linearity, the lower limit of detection and intra-assay variation, three replicates of nine 10 fold dilutions of *B. anthracis, Y. pestis* and *F. tularensis* DNA in TE buffer (Tris 10 mM, EDTA 1 mM; adjusted to ph 8.0 with HCl) containing approximately 10 ng to 0.1 fg DNA were analyzed by the method of Example 2. Standard graphs of the Ct values were compiled and the correlation coefficients were calculated. All R2 values were above 0.99 and slopes were near 3.3 thus making PCR amplification effiency highly successful.

The sensitivity of the real-time PCR analysis of the invention for *B. anthracis* pagA gene and capB gene was 1 fg and 10 fg, respectively, for *Y. pestis* pla gene 0.1 fg and for *F. tularensis* 23 kDa gene sensitivity was 0.1 fg of total DNA. The sensitivity of the method of invention corresponds to 1 bacterial cell with all three category A agents.

For assessing the specificity of the real-time PCR assay of the invention the clinical and environmental samples (Table 1) were analyzed to represent the overall diversity of bacterial phylogenetic tree. The main lines of bacterial phylogenetic tree were excluded based on the absence of their habitat at normal sample collection sites, e.g. the deep sea thermophilic bacteria. From each branch of the tree one species was chosen to represent the whole group.

The real-time PCR analysis was performed as described in Example 2. At least 1 ng of total DNA was loaded per reaction to detect possible cross-reaction with non-specific targets. All samples were analyzed in duplicate.

Detectable amplification was observed only from control strains of *B. anthracis, Y. pestis* and *F. tularensis* (Sterne 7702, ATCC 4229, LVS, EV76-c) and the specific clinical *F. tularensis* samples (see Example 4). Non-specific amplification products were not detected. Furthermore, internal positive con-trots (IPC's) were successfully amplified in all assays and thus no samples were discarded from analysis or had to be re-run based on possible inhibitorial factors.

Example 4

Analysis of the Clinical Samples

Clinical animal tissue samples from a cow with anthrax and a hare with tularemia were received from the National Veterinary and Food Research Institute, University of Helsinki and Oulu, respectively.

DNA from formaldehyde-fixed infected cow tissue (20 mg) and paraffin embedded hare tissue (10×40 μm) were purified with the QiaAmp DNA miniKit (Qiagen, Hilden, Germany) as suggested by the manufacturer.

Three separate DNA isolations were made from the samples and the samples were analysed on duplicate by the real time PCR assay as described in Example 2.

Figure 3:
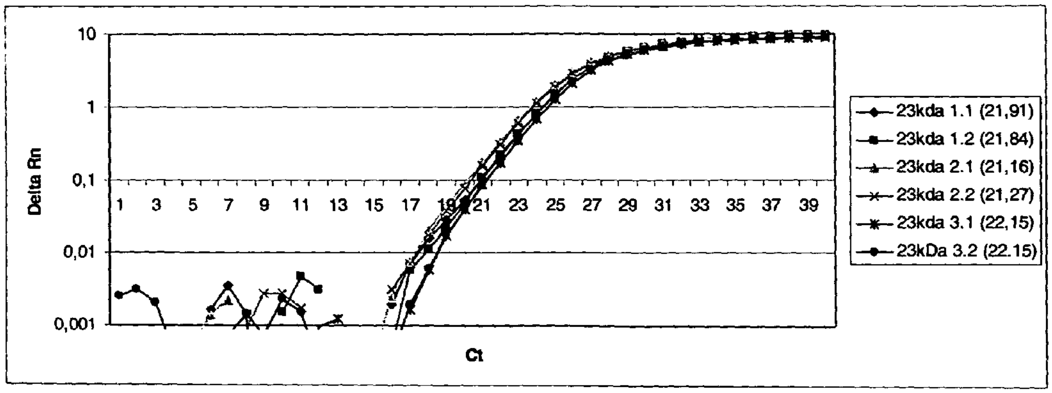
FIG. 3 shows a real time PCR analysis of a tissue sample from an infected hare using ABI 7300 Taqman-MGB assay targeting the 23 kDa gene of *F. tularensis*. Three separate isolations (1, 2, and 3) were run in duplicates. Ct values are shown on the right.

The Ct values of these samples ranged from 16-20 and 21-22 Ct's, respectively (FIGS. 2 and 3) thus giving strong positive signals at early stages of the run.

Figure 4:
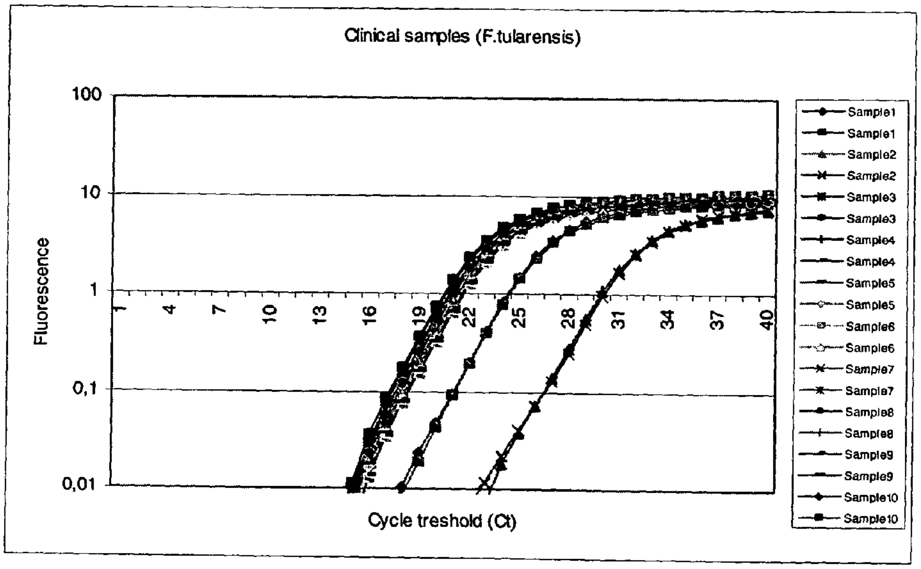
FIG. 4 shows a real time PCR analysis of ten clinical *F. tularensis* isolates using ABI 7300 Taqman-MGB assay targeting the 23 kDa gene of *F. tularensis*.

Additionally, the clinical *F. tularensis* isolates (samples no. 21-30) from the collections of Haartman Institute, Division of Bacteriology and Immunology, Helsinki, Finland were analysed by the real time PCR assay as described in Example 2. As expected all samples gave a positive signal. The results are shown in FIG. 4.

Example 5

Construction of a Control Plasmid

For the real-time PCR analysis method a control plasmid, to be used without a risk of infection, is constructed by inserting the gene regions of the *B. anthracis* pagA and capB genes having sequences of SEQ ID NOS: 21 and 22, respectively, the *Y. pestis* pla gene having the sequence of SEQ ID NO: 23 and the *F. tularensis* 23 kDa gene having the sequence of SEQ ID NO: 24 (shown in Table 3) into a plasmid. The gene regions are amplified in a traditional PCR using species-specific primers that include sites for the restrictions enzymes (Table 2). The amplified gene regions are separately cloned to the *E. coli* vector pUC19 multiple cloning site. Subsequently the four different plasmids are combined by restriction and ligation reactions according to methods commonly used in molecular biology. The resulting plasmid is a non-infectious plasmid, which contains all four gene regions. The plasmid can thus be used as a positive control for all the primers of the invention.

The invention claimed is:

1. A method for simultaneously detecting the presence or absence of *Bacillus anthracis, Yersinia pestis* and *Francisella tularensis* in a sample, the method comprising:

obtaining DNA from the sample;

performing a single real time PCR assay run using species-specific Taqman MGB probes and species-specific primers; and detecting fluorescence of the probes;

wherein:

the forward and reverse primers for *B. anthracis* have the sequences of SEQ ID NOS: 1 and 2, respectively, derived from the pagA gene and SEQ ID NOS: 4 and 5, respectively, derived from the capB gene, the forward and reverse primers for *Y. pestis* have the sequences of SEQ ID NOS: 7 and 8, respectively, derived from the pla gene, the forward and reverse primers for *F. tularensis* have the sequences of SEQ ID NOS: 10 and 11, respectively, derived from the 23 kDa gene, the concentrations of said forward primers and said reverse primers are optimized in the range of 50-900 nM under the same temperature parameters, the specific Taqman MGB probe comprises a sequence selected from the group of full-length sequences set forth in SEQ ID NOS: 3, 6, 9, and 12.

2. A method of claim 1 wherein the optimal conditions in the real time PCR assay are for *B. anthracis* 300 nM forward primer, 900 nM reverse primer and 250 nM of Taqman MGB probe, for *Y. pestis* 50 nM forward primer, 300 nM reverse primer and 250 nM of Taqman MGB probe, and for *F. tularensis* 300 nM forward primer, 900 nM reverse primer and 250 nM of Taqman MGB probe.

3. A method of claim 1 wherein a multiplex PCR-format is used, and the reactions are performed in a single assay tube using differently labeled Taqman MGB probes.

4. The method according to claim 1, wherein the optimal conditions in the real time PCR assay are for *B. anthracis* 300 nM forward primer, 900 nM reverse primer and 250 nM of Taqman MGB probe, for *Y. pestis* 50 nM forward primer, 300 nM reverse primer and 250 nM of Taqman MGB probe, and for *F. tularensis* 300 nM forward primer, 900 nM reverse primer and 250 nM of Taqman MGB probe.

5. The method according to claim 1, wherein a multiplex PCR-format is used, and the reactions are performed in a single assay tube using differently labeled Taqman MGB probes.

6. The method according to claim 2, wherein a multiplex PCR-format is used, and the reactions are performed in a single assay tube using differently labeled Taqman MGB probes.

7. The method according to claim 4, wherein a multiplex PCR-format is used, and the reactions are performed in a single assay tube using differently labeled Taqman MGB probes.

8. The method of claim 1, wherein the sample is a bacterial culture, a tissue fragment, a secretion sample, a blood sample, a clinical sample from a lumbar puncture or abscesses, obtained from a patient.

9. The method of claim 1, wherein the sample is an environmental sample, a paper sample, or an air sample collected from the site to be examined.

* * * * *